United States Patent [19]
Horn et al.

[11] Patent Number: 5,306,798
[45] Date of Patent: Apr. 26, 1994

[54] TRANSPARENT, AUTOCLAVABLE, NON-CYTOTOXIC, ESSENTIALLY COMPACT POLYURETHANE EMBEDDING COMPOSITIONS, THE PREPARATION THEREOF AND THE USE THEREOF, ESPECIALLY FOR ARTICLES USED IN MEDICINE

[75] Inventors: Peter Horn, Heidelberg; Werner Hinz, Frankenthal; Georg Knoblauch, Munich; Falko Ramsteiner, Ludwigshafen; Gottfried Knorr, Schwarzheide, all of Fed. Rep. of Germany

[73] Assignee: BASF Aktiengesellschaft, Ludwigshafen, Fed. Rep. of Germany

[21] Appl. No.: 970,749

[22] Filed: Nov. 2, 1992

[30] Foreign Application Priority Data

Oct. 21, 1991 [DE] Fed. Rep. of Germany ....... 4134693

[51] Int. Cl.$^5$ .............................. C08G 18/32
[52] U.S. Cl. ....................... 528/58; 528/59; 528/60; 528/71; 528/74.5; 528/77
[58] Field of Search ............... 528/58, 59, 60, 71, 528/74.5, 77

[56] References Cited

U.S. PATENT DOCUMENTS 4,742,112  5/1988  Brauer et al. .................. 528/49

FOREIGN PATENT DOCUMENTS 0045393  7/1981  European Pat. Off. .

Primary Examiner—Maurice J. Welsh
Attorney, Agent, or Firm—Dennis V. Carmen

[57] ABSTRACT

The invention relates to transparent, autoclavable, non-cytotoxic, essentially compact polyurethane embedding compositions which are prepared by reacting a) modified diphenylmethane diisocyanates with
b) compounds with at least two reactive hydrogens, which contain or are composed of
   b1) at least one polyether-polyol with an average functionality of from 3 to 8, a hydroxyl number of from 200 to 1000 and an alkali metal ion content of from 150 to 1200 ppm or, preferably, a mixture of (b1) and castor oil and/or at least one polyether-polyol (b2) with a functionality of from 2 to 3, a hydroxyl number of from 90 to 200 and an alkali metal ion content of less than 10 ppm in the presence or absence of
c) catalysts and to a process for preparing the polyurethane embedding compositions and to the use thereof for articles used in medicine.

22 Claims, No Drawings

TRANSPARENT, AUTOCLAVABLE, NON-CYTOTOXIC, ESSENTIALLY COMPACT POLYURETHANE EMBEDDING COMPOSITIONS, THE PREPARATION THEREOF AND THE USE THEREOF, ESPECIALLY FOR ARTICLES USED IN MEDICINE

The present invention relates to transparent, autoclavable, non-cytotoxic, essentially compact polyurethane, which is also abbreviated to PU hereinafter, embedding compositions which are prepared by reacting a) modified diphenylmethane diisocyanates with
b) compounds with at least two reactive hydrogens in the absence or, preferably, presence of
c) catalysts where component (b) is
   b1) at least one polyether-polyol with an average functionality of from 3 to 8, a hydroxyl number of from 200 to 1000 and an alkali metal ion content of from 150 to 1200 ppm or a mixture which contains (b1) and
   b2) castor oil and/or at least one polyether-polyol with a functionality of from 2 to 3, a hydroxyl number of from 90 to 200 and an alkali metal ion content of less than 10 ppm.

PU casting systems are known and are reviewed, for example, in the Kunststoff-Handbuch "Polyurethane", Volume 7, 2nd edition, 1983, pages 392 et seq., edited by Dr. G. Oertel, published by Carl Hanser, Munich, Vienna.

The use of PU embedding compositions for producing moldings for medical equipment, especially as embedding material for hollow fibers in dialyzers, is likewise not novel and is recommended as advantages because of the ease of manipulation of PU embedding compositions and their lower degree of shrinkage during curing. Examples of PU formulations disclosed specifically for embedding hollow fibers are indicated below.

U.S. Pat. No. 3,962,094 describes catalyst-free embedding compositions of castor oil/4,4'-MDI, -toluylene diisocyanate or -phenylene diisocyanate prepolymers with terminal NCO groups and of a crosslinker which contains castor oil and/or an ester of an at least tetrahydric alcohol and a hydroxyl- or epoxy-containing aliphatic carboxylic acid of at least 12 carbons.

According to the statements in DE-A 2 749 491 (U.S. Pat. No. 4,170,559), the catalyst-free embedding compositions are composed of a prepolymer prepared from castor oil and polyoxypropylene glycol and 4,4'-MDI, and of a crosslinker based on an ester of an alcohol with 2 or 3 hydroxyl groups and of an aliphatic carboxylic acid of at least 12 carbons, with one or more hydroxyl and/or epoxy groups. Polyisocyanates also mentioned as suitable for preparing the prepolymers are: 2,4- and 2,6-toluylene diisocyanate or phenylene diisocyanate. Also suitable as crosslinkers are monoesters and/or diesters of ethylene glycol and ricinoleic acid, trimethylolpropane or -ethane.

Physiologically acceptable PU molding compositions, in particular for embedding hollow fibers in dialyzers, are prepared, according to the statements in DD-A-251,565, by reacting highly reactive, low-viscosity and stable co-prepolymers composed of solid, highly reactive aromatic diisocyanates and less reactive liquid diisocyanates in the ratio of from 1:5 to 5:1 by weight, and polyols, with polyols from the group comprising castor oil and/or its transesterification products, highly pure polyesters and polyoxytetramethylene glycol. PU embedding compositions composed of a PU prepolymer having isocyanate end groups and of a polyol mixture containing N,N,N',N'-tetrakis(2-hydroxypropyl)ethylenediamine are disclosed in U.S. Pat. No. 4,224,164. According to the statements in U.S. Pat. No. 4,742,112, the polyol component used for preparing PU embedding compositions for electrical equipment comprises mixtures of from 10 to 60% by weight of a ricinoleic ester and from 90 to 40% by weight of a $C_2$–$C_6$-hydrocarbon polymer with at least one hydroxyl group. Two-component PU formulations which are not cytotoxic in the cured state and are suitable as embedding compositions for separating apparatus are composed, according to DE-A-3 048 529 (U.S. Pat. No. 4,332,927), of at least one NCO-terminated prepolymer, of at least one polyol and of a catalytic amount of a dicarboxylated dialkyltin compound. PU embedding compositions catalyzed with tin-sulfur compounds for embedding cellulose hollow fibers in dialyzers are described in DD-A-155,777.

The abovementioned PU embedding compositions can be used to produce equipment used in medicine or moldings therefor and be sterilized with ethylene oxide and/or with γ rays before use. However, the disadvantages of these types of sterilization are that remaining traces of ethylene oxide may induce allergies in some patients, and the γ rays may produce unidentifiable cleavage products so that it is not possible completely to rule out a certain risk to the health of the patient caused by the dialysis. Prior art embedding compositions are, furthermore, insufficiently resistant to heat and chemicals so that they cannot be autoclaved at 121° C. for 20 minutes.

Another serious disadvantage is that the known PU embedding compositions cannot be processed together with every type of fiber. Thus, for example, cellulose fibers are attacked and damaged by PU embedding compositions based on castor oil. In addition, difficulties frequently arise during the manufacturing process with prior art PU embedding composition systems. Although it is possible for the embedding compositions to be cut immediately after the embedding and for about 30 minutes thereafter, they then harden very rapidly so that the moldings, preferably dialysis filters, cannot be cut after only 24 hours. These disadvantageous characteristics cause, in particular, when there are breaks in production, losses of product at the end of the process. If components in the PU formulations used to prepare the PU embedding compositions contain primary, secondary and/or tertiary amino groups and reactive hydrogen atoms, the resulting embedding compositions are unstable to sterilization with peracetic acid.

To overcome these disadvantages, EP-A-0 393 545 and EP-A-0 413 265 describe transparent, autoclavable, essentially compact PU embedding compositions which are prepared using diphenylmethane diisocyanates (MDIs) modified with selected compounds. According to the statements in EP-A-0 393 545, suitable modified MDIs which are liquid at 23° C. are prepared by reacting an MDI isomer mixture which is composed of from 60 to 90% by weight 4,4'-MDI, from 40 to 8% by weight 2,4'-MDI and from 0 to 5% by weight 2,2'-MDI with a glycerol- and/or trimethylolpropane-started polyoxypropylene-polyol with a molecular weight of from 350 to 800. EP-A-0 413 265 describes the use of modified MDIs obtained by reacting 4,4'-MDI or 2,4'-

MDI or MDI isomer mixtures with selected specific, at least tetrafunctional polyoxypropylenepolyols and/or polyoxypropylene/polyoxyethylene-polyols containing up to 80% by weight of polymerized ethylene oxide units for preparing PU embedding compositions. PU embedding compositions prepared from the abovementioned components have increased heat resistance and improved hydrolysis resistance. It is furthermore advantageous that the maximum curing temperature which is reached due to the heat liberated in the polyaddition reaction can be distinctly reduced. However, it has also emerged that there may be problems of adhesion between PU embedding compositions and other materials such as polycarbonates following repeated sterilization. For example, the PU embedding compositions may become detached from the dialyzer housing. This detachment occurred especially when, owing to faults in the autoclaving, the temperature exceeded 121° C. and/or the sterilization time exceeded 20 minutes.

It is an object of the present invention to improve the known PU embedding compositions, preferably those described in EP-A-0 393 545 and EP-A-0 413 265, by suitable measures. The aim particularly is to improve the adhesion between PU embedding compositions and other materials so that there is no detachment of the PU embedding compositions if there are at least short-term faults in the sterilization.

We have found that this object is achieved by exclusive or partial use of alkali metal-containing, at least trifunctional polyether-polyols for preparing the PU embedding compositions.

The present invention thus relates to transparent, autoclavable, non-cytotoxic, essentially compact polyurethane embedding compositions, which are prepared by reacting
a) modified diphenylmethane diisocyanates with
b) compounds with at least two reactive hydrogens in the presence or absence of
c) catalysts wherein component (b) is composed of or contains at least one polyether-polyol (b1) with an average functionality of from 3 to 8, a hydroxyl number of from 200 to 1000 and an alkali metal ion, preferably potassium ion, content of from 150 to 1200 ppm.

The present invention also relates to a process for preparing the transparent, autoclavable, non-cytotoxic, essentially compact PU embedding compositions as claimed in claim 18 and to the use of the PU embedding compositions for embedding hollow fibers, preferably composed of polysulfones or polycarbonates, in dialysis equipment, for producing articles used in medicine, and for bonding bioceramic coatings to endoprostheses as claimed in claim 22.

The PU embedding compositions according to the invention are transparent, non-cytotoxic and not only do they have improved adhesion to other materials, eg. polycarbonates, at elevated temperatures over a lengthy period, but also the reaction mixtures can be used for embedding without foam formation. The PU embedding compositions can be cut after only 2 hours, but the rate of hardening is such that they can still be cut after more than 24 hours. It is furthermore advantageous that the PU embedding compositions according to the invention can be processed with all conventional types of hollow fibers, eg. cupro, polysulfone, polycarbonate or cellulose fibers, and the polycarbonates do not need, before processing, to be treated by corona discharge to improve the adhesion. The PU embedding compositions are stable to percarboxylic acids so that moldings made from such PU embedding compositions can be sterilized with peracetic acid.

The following relates to starting components (a) to (c) which can be used to prepare the PU embedding compositions according to the invention:

a) Suitable modified diphenylmethane diisocyanates, normally abbreviated to MDI, expediently have a viscosity of from 100 to 8000 mPa.s, preferably from 500 to 3000 mPa.s at 23° C., and an NCO content of from 29 to 15% by weight, preferably from 26 to 15% by weight and, in particular, from 24 to 17% by weight, based on the total weight, and are prepared by conventional processes by reacting 4,4'-MDI or 2,4'-MDI or MDI isomer mixtures, expediently those composed of from 20 to 90, preferably from 50 to 82, % by weight 4,4'-MDI, from 80 to 8, preferably from 50 to 8, % by weight 2,4'-MDI and from 0 to 5, preferably from 0 to 3, % by weight 2,2'-MDI with at least one polyoxypropylene-polyol, at least one polyoxypropylene/polyoxyethylene-polyol or a mixture of at least one polyoxypropylene-polyol and at least one polyoxypropylene/polyoxyethylene-polyol in the ratio of NCO to OH groups of from 2.5:1 to 15:1, preferably from 5:1 to 10:1, expediently at from 50° to 100° C., preferably from 60° to 90° C., in a reaction lasting from 0.5 to 3 hours, preferably from 1 to 2 hours. Modification of the MDIs with urethane groups by partial reaction of isocyanate groups with hydroxyl groups is carried out using commercial polyoxypropylene-, polyoxypropylene/polyoxyethylene- or polyoxyethylene/polyoxypropylene-polyols which normally have an; alkali metal content of less than 10 ppm, preferably of less than 5 ppm. Besides the abovementioned polyoxyalkylenepolyols, it is also possible to use as sole modifying agent, or mixed with polyoxypropylene- and/or polyoxypropylene/polyoxyethylene-polyols and/or polyoxyethylene/polyoxypropylene-polyols, either dipropylene glycol or castor oil or mixtures of dipropylene glycol and castor oil.

Examples of polyoxypropylene-polyols for modifying the MDIs are polyoxypropylene glycols with a hydroxyl number of up to 400, mixtures of dipropylene glycol and polyoxypropylene glycols with a hydroxyl number of up to 400, polyoxypropylenepolyols which have been started with glycerol, trimethylolpropane or a mixture of glycerol and trimethylolpropane and have a hydroxyl number of from 480 to 210, polyoxypropylene-polyols which have been started with sucrose or sorbitol or mixtures of sucrose and sorbitol and have a hydroxyl number of from 250 to 380, and of polyoxypropylene/polyoxyethylene-polyols are polyoxypropylene/polyoxyethylene-polyols which have been started with sucrose or sorbitol or mixtures of sucrose and sorbitol and contain from 1 to 80, preferably from 10 to 50, % by weight, based on the total weight of the alkylene oxide units, of polymerized ethylene oxide units, and have a hydroxyl number of from 230 to 500. In place of sucrose and/or sorbitol, it is also possible to use, for preparing the polyoxypropyleneor polyoxypropylene/polyoxyethylene-polyols, mixtures of said starter molecules and at least one costarter from the group comprising water, propylene glycol, glycerol and trimethylolpropane, where the amount of costarter is expediently only such that the functionality of the resulting polyoxyalkylenepolyols is not less than 4.

MDIs modified in this way are described in EP-A-0 393 545 and EP-A-0 413 265 so that these patent publications are to be regarded as part of the description.

However, modified MDIs which are preferably used are NCO prepolymers which contain bonded urethane groups and have an NCO content of from 24 to 15% by weight, preferably from 22 to 17% by weight, and which are prepared by reacting, based on the total weight, at least 85% by weight, preferably from 90 to 96% by weight, of an NCO-containing prepolymer with an NCO content of from 29 to 21% by weight, preferably from 26 to 22% by weight, which in turn is prepared by reacting 4,4'-MDI with dipropylene glycol or at least one polyoxypropylene glycol with a hydroxyl number of up to 400, preferably from 50 to 250, or a mixture of dipropylene glycol and at least one polyoxypropylene glycol with a hydroxyl number of up to 400 and a maximum of 15% by weight, preferably from 4 to 10% by weight, of castor oil or a maximum of 15% by weight of a polyoxyalkylene-polyol which has been started with glycerol, trimethylolpropane or a mixture of glycerol and trimethylolpropane and has a hydroxyl number of from 90 to 200 and an alkali metal ion content of less than 10 ppm from the group comprising polyoxypropylene-, polyoxypropylene/polyoxyethylene- and polyoxyethylene/poly-oxypropylene-polyols.

b) The compounds with at least two reactive hydrogens used according to the invention are polyether-polyols with a very high alkali metal ion content compared with commercial products. It is possible to use according to the invention polyether-polyols (b1) or mixtures thereof with an average functionality of from 3 to 8, preferably from 3 to 6, a hydroxyl number from 200 to 1000, preferably from 230 to 970 and, in particular, from 350 to 750, and an alkali metal ion, preferably potassium ion, content of from 150 to 1200 ppm, preferably from 200 to 1000 ppm and, in particular, from 400 to 600 ppm.

The component (b) used to prepare the PU embedding compositions according to the invention can be exclusively polyether-polyols (b1) with these alkali metal ion contents. However, outstandingly suitable as component (b) are also mixtures, so that these are preferably used, which contain b1) at least one polyether-polyol (b1) with the abovementioned specification and b2) castor oil or at least one polyether-polyol with a functionality of from 2 to 3, preferably from 2.3 to 3, a hydroxyl number of from 90 to 200, preferably from 120 to 180 and, in particular, from 130 to 160 and an alkali metal ion content of less than 10 ppm, preferably less than 5 ppm, or mixtures of castor oil and such polyether-polyols (b2) with a low alkali metal ion content. Particularly suitable mixtures of (b1) and (b2) contain, based on the total weight, or are preferably composed of, from 1 to 20% by weight, preferably from 1 to 15% by weight, of at least one polyether-polyol (b1) and from 99 to 80% by weight, preferably from 99 to 85% by weight, of castor oil and/or at least one polyether-polyol (b2).

Polyether-polyols (b1) with alkali metal ion contents of from 150 to 1200 ppm which can be used are the conventional polyether-polyols with an average functionality of from 3 to 8 and a hydroxyl number of from 200 to 1000, with the proviso that the polyether-polyols are prepared directly with the alkali metal ion content necessary according to the invention or, preferably, the alkali metal ion content of commercial polyether-polyols, which is normally below 10 ppm, is increased by a suitable method. It is possible for this purpose to treat the polyether-polyols with aqueous alkali metal hydroxide, preferably an aqueous potassium hydroxide solution, or alcoholic alkali metal alcoholate solutions, preferably alcoholic potassium alcoholate solutions, in the required amounts at room temperature or elevated temperatures, eg. from 20° to 120° C. After this, the water or alcohol which has been added and formed is removed by distillation at from 70° to 110° C., if necessary under reduced pressure, eg. from 0.01 to 1 mbar.

Examples of polyether-polyols (b1) which are preferably used are trimethylolpropane-started polyoxyethylene-polyols with a hydroxyl number in the range from 632 to 970 and a potassium ion content in the range from 400 to 600 ppm and polyoxypropylene-polyols which have been started with glycerol or trimethylolpropane or a glycerol/trimethylolpropane mixture and which have a hydroxyl number in the range from 210 to 480 and a potassium ion content in the range from 400 to 600 ppm. Examples of polyether-polyols with a high alkali metal content which are also suitable are polyoxypropylene-polyols with an average functionality of from 4 to 8, preferably from 4 to 6, and a hydroxyl number of from 230 to 500, preferably from 250 to 380, which are obtained using sucrose or, preferably, sorbitol or mixtures of sucrose and sorbitol as starters, possibly also using as costarters water, propylene glycol, glycerol or mixtures of at least two of said costarters, with the proviso that the polyether-polyols have an alkali metal ion content, preferably potassium ion content, of from 200 to 1000 ppm, preferably from 400 to 700 ppm. Also suitable are polyoxypropylene- and/or polyoxyethylene-polyols with an alkali metal ion content of from 150 to 800 ppm and a hydroxyl number of from 50 to 750, which can be obtained by reacting pentaerythritol or a mixture of pentaerythritol and glycerol and/or trimethylolpropane, expediently in a molar ratio of pentaerythritol to glycerol and/or trimethylolpropane of 1:1, with propylene oxide or ethylene oxide. Polyether-polyols with a high alkali metal content which can also be used are polyoxypropylene/polyoxyethylene-polyols which are obtained, for example, by polyaddition of propylene oxide and ethylene oxide in a molar ratio of from 1:1 to 1:8, preferably from 1:1 to 1:3, onto glycerol, trimethylolpropane, a mixture of glycerol and trimethylolpropane as starters, with a hydroxyl number of from 350 to 950, preferably from 380 to 600, and an alkali metal ion content, preferably potassium ion content, of from 200 to 800 ppm, preferably from 400 to 600 ppm, or by polyaddition of propylene oxide and ethylene oxide in a molar ratio of from 1:1 to 1:8, preferably from 1:1 to 1:3, onto sucrose or, preferably, sorbitol or mixtures of sucrose and sorbitol as starters, with a hydroxyl number of from 200 to 500, preferably from 230 to 300, and an alkali metal ion content, preferably potassium ion content, of from 200 to 800 ppm, preferably from 400 to 600 ppm. The polyether-polyols (b1) which are mentioned by way of example can be used singly or in the form of mixtures.

As already mentioned, it is possible to use as component (b2) of the mixture of (b1) and (b2) castor oil. However, also suitable are polyetherpolyols with an alkali metal content less than 10 ppm, eg. polyoxypropylenepolyols, polyoxyethylene/polyoxypropylene-polyols with a content of terminal propylene oxide units of from 1 to 15% of the total weight of the alkylene oxide units, or, preferably, polyoxypropylene/polyoxyethylene-polyols with a content of ethylene oxide units of from 60 to 90% of the total weight of the alkylene oxide units. Preferably used are trifunctional, in particular glycerol- or trimethylolpropane-started polyether-polyols, eg. polyoxypropylene-, polyoxypropylene/-polyoxyethylene-polyols or polyoxyethylene/polyoxy-propylene-polyols with a hydroxyl number of from 120 to 180 and an alkali metal ion content of less than 5 ppm.

The PU embedding compositions according to the invention can be prepared without using at least trifunctional crosslinkers. However, where crosslinkers are employed to modify the mechanical properties, expediently used are hydroxyl-containing crosslinkers with a functionality of from 3 to 8, preferably from 3 to 4. Examples of suitable crosslinkers are alcohols with 3 or more hydroxyl groups, eg. glycerol, trimethylolpropane, pentaerythritol, 2,2,6,6-tetrahydroxymethyl-4-oxa-1,7-heptanediol (dipentaerythritol), tripentaerythritol, 3,3,7,7-tetrahydroxymethyl-5-oxanonane(di-trimethylolpropane) and sorbitol, and the low molecular weight polyoxypropylene-, polyoxyethylene- or polyoxypropylene/polyoxyethylene-polyols started with these alcohols.

c) The PU embedding compositions according to the invention can be prepared in the absence or presence of catalysts. However, the PU embedding compositions are preferably prepared in the presence of catalysts which greatly increase the rate of the reaction of the modified diphenylmethane diisocyanates (a) with the hydroxyl-containing compounds with at least two reactive hydrogens (b). Suitable catalysts are organometallic compounds, preferably organic tin compounds such as tin(II) salts of organic carboxylic acids, eg. tin(II) diacetate, tin(II) dioctanoate, tin(II) diethylhexanoate and tin(II) dilaurate, and the dialkyltin(IV) salts of organic carboxylic acids, eg. dibutyltin diacetate, dibutyltin dilaurate, dibutyltin maleate and dioctyltin diacetate. Catalysts of this type are described, for example, in DE-A-3 048 529. Dialkyltin(IV) mercapto compounds have also proven to be suitable, eg. dilauryltin(IV) dimercaptide, as have compounds of the formula R₂Sn(SR'-O-CO-R")₂ or R₂Sn(SR'-CO-OR")₂ where R is alkyl of at least 8 carbons, R' is alkylene of at least 2 carbons and R" is alkyl of at least 4 carbons. Examples of catalysts of this type, which are described, for example, in DD-A-218 668, are dioctyltin bis(thioethylene glycol 2-ethylhexanoate), dioctyltin bis(thioethylene glycol laurate), dioctyltin bis(2-ethylhexyl thiolatoacetate), dioctyltin bis(hexyl thiolatoacetate) and dioctyltin bis(lauryl thiolatoacetate). Other catalysts which have proven very useful are organotin compounds with tin-oxygen or tin-sulfur bonds as described, for example, in DD-A-255 535, of the formula (R₃Sn)₂O, R₂SnS, (R₃Sn)₂S, R₂Sn(SR')₂ or RSn(SR')₃ where R is alkyl of 4 to 8 carbons and R' is alkyl of 4 to 12 carbons, and R' can also be —R"COOR''', and —R"OCOR''', where R" is alkyl of 1 to 6 carbons and R''' is alkylene of 4 to 12 carbons. Examples of these are bis(-tributyltin) oxide, dibutyltin sulfide, dioctyltin sulfide, bis(tributyltin) sulfide, dibutyltin bis(2-ethylhexyl thioglycolate), dioctyltin bis(2-ethylhexyl thioglycolate), octyltin tris(2-ethylhexyl thioglycolate), dioctyltin bis(thioethylene glycol 2-ethylhexanoate) and dibutyltin (thioethylene glycol laurate). Preferably used as catalysts are mono-n-octyltin tris(2-ethylhexyl thioglycolate), di-n-octyltin bis(2-ethylhexyl thioglycolate) and dibutyltin dilaurate.

The organometallic compounds can be employed as catalysts either singly or in combinations. Particularly advantageous combinations are composed of, based on the total weight, from 1 to 99% by weight of mono-n-octyltin tris(2-ethylhexyl thioglycolate) and from 99 to 1% by weight of di-n-octyltin bis(2-ethylhexyl thioglycolate) or 94% by weight of di-n-octyltin bis(2-ethylhexyl thioglycolate) and 6% by weight of mono-n-octyltin tris(2-ethylhexyl thio-glycolate).

The catalysts are normally used in an amount of from 0.001 to 0.2 part by weight, preferably from 0.005 to 0.015 part by weight, per 100 parts by weight of component (b).

The PU embedding compositions according to the invention are prepared by reacting the modified MDIs (a) and compounds with at least two reactive hydrogens (b), preferably in the presence of the catalysts (c), in amounts such that the ratio of NCO groups in the modified MDIs (a) to the total of reactive hydrogens in component (b) is from 0.9 to 1.3:1, preferably from 0.95 to 1.2:1 and, in particular, from 1.0 to 1.1:1. For this, the essentially completely degassed starting components are vigorously mixed at, expediently, from 18° to 70° C., preferably from 22° to 60° C. The reaction mixtures, which have a total alkali metal ion, preferably potassium ion, content of, preferably, from 8 to 110 ppm, in particular from 15 to 50 ppm, are introduced into a suitable mold and left to cure for from 0.3 to 4 hours, preferably from 1 to 3 hours.

As already explained, the transparent, autoclavable, non-cytotoxic, essentially compact PU embedding compositions are used, in particular, for embedding hollow fibers such as cupro fibers and preferably polysulfone, polycarbonate fibers or cellulose hollow fibers in dialyzers, where the dialysis equipment, in particular the sleeve for the dialysis filter, is expediently composed of a polycarbonate based on bisphenol A.

The PU embedding compositions according to the invention are also suitable for producing articles used in medicine and for bonding bioceramic coatings to endo-prostheses.

The PU embedding compositions are non-cytotoxic, transparent, do not interact with the hollow fibers, adhere strongly to the polycarbonate and can be cut readily without damaging the embedded hollow fibers.

EXAMPLE 1

Preparation of the Modified MDI 93.99 parts by weight of a urethane-containing MDI prepolymer with an NCO content of 23% by weight, which had been prepared by reacting 4,4'-MDI with a mixture of dipropylene glycol and a polyoxypropylene glycol with a hydroxyl number of 250 and a potassium ion content of 3 ppm in a ratio 1:0.6 by weight, were heated to 60° C. with stirring and mixed dropwise over the course of 30 minutes with 6.01 parts by weight of castor oil which had a water content of 0.03% by weight. The reaction mixture was heated at 80° C. for one hour, when the reaction was complete.

The resulting MDI mixture modified with urethane groups had an NCO content of 20.5% by weight and a viscosity of 2100 mPa.s at 25° C.

EXAMPLE 2

Preparation of the PU Embedding Composition

A Component

Mixture of 5 parts by weight of a polyether-polyol with a hydroxyl number of 931 and a potassium ion content of 508 ppm, prepared by addition of ethylene oxide onto trimethylolpropane as starter in the presence of potassium hydroxide as catalyst, 94.95 parts by weight of castor oil and 0.05 parts by weight of a catalyst composed of, based on the total weight, 94% by weight di-n-octyltin bis(2-ethylhexyl thioglycolate) and 6% by weight mono-n-octyltin tris(2-ethylhexyl thioglycolate).

B Component modified MDI mixture from Example 1

100 parts by weight of A component and 77.7 parts by weight of B component, corresponding to an NCO index of 105, were vigorously mixed at 23° C.; the reaction mixture was poured into a mold and left to cure.

The reaction mixture had a potassium ion content of 25.4 ppm and a gel time of 350 seconds.

The molding had a Shore A hardness of 96.5 after storage at 23° C. for 24 hours.

EXAMPLE 3

A component: similar to Example 2 but using the starting materials in the following amounts 5.2 parts by weight of the polyether-polyol with a hydroxyl number of 931 and a potassium ion content of 508 ppm, 94.7 parts by weight of castor oil and 0.1 part by weight of the catalyst.

B component: modified MDI mixture from Example 1

100 parts by weight of the A component at 40° C. and 77.7 parts by weight of the B component at 40° C., corresponding to an NCO index of 105, were mixed in a low-pressure machine, and the reaction mixture, which had a potassium ion content of 26.4 ppm, was centrifuged at 40° C. for 5 minutes.

The molding produced by the centrifugal process was bubble-free and dry immediately after demolding and could be cut after 2 hours.

It was possible to autoclave dialyzers produced from polycarbonate sleeves, polysulfone hollow fibers and the PU embedding compositions at 121° C. at least 6 times without damage to the molding. The cytotoxicity tests specified in the International Standards Organization Guideline ISO/TR 7405-1984(E) "Biological Evaluation of Dental Materials" and the provisional standard DIN V 13930, Sept. 1990 "Biologische Prüfungen von Dentalwerkstoffen" were passed.

Furthermore, storage of the molding at 23° C. in 7% by weight aqueous peracetic acid for 10 days showed no decrease in the peracetic acid content.

EXAMPLE 4

Preparation of the Modified MDI 2781.85 parts by weight of a urethane-containing MDI prepolymer with an NCO content of 23% by weight, which was prepared by reacting 4,4'-MDI with a mixture of dipropylene glycol and a polyoxypropylene glycol with a hydroxyl number of 250 and a potassium ion content of 3 ppm in the ratio 1:0.6 by weight, were heated to 60° C. with stirring and mixed dropwise, over the course of 30 minutes, with 219.83 parts by weight of a trimethylolpropane-started polyoxypropylene-polyol with an OH number of 148.5 and a potassium ion content of 3 ppm. The reaction mixture was heated at 80° C. for one hour, when the reaction was complete.

The resulting MDI mixture modified with urethane groups had an NCO content of 20.3% by weight and a viscosity of 3324 mPa.s at 25° C.

EXAMPLE 5

Preparation of the PU Embedding Composition

A Component

Mixture of 7.3 parts by weight of a polyether-polyol with a hydroxyl number of 923 and a potassium ion content of 534 ppm, prepared by addition of ethylene oxide onto trimethylolpropane as starter in the presence of potassium hydroxide as catalyst, 92.65 parts by weight of a trimethylolpropane-started polyoxypropylene-polyol with an OH number of 148.5 and a potassium ion content of 3 ppm and 0.05 part by weight of a catalyst composed, based on the total weight, of 94% by weight of di-n-octyltin bis(2-ethylhexyl thioglycolate) and 6% by weight of mono-n-octyltin tris(2-ethylhexyl thioglycolate)

B component: MDI mixture modified with urethane groups from Example 4

100 parts by weight of A component and 79.18 parts by weight of B component, corresponding to an NCO index of 105, were vigorously mixed at 23° C.; the reaction mixture was poured into a polystyrene beaker and left to cure.

The reaction mixture had a potassium ion content of 39 ppm and a gel time of 203 seconds.

The produced molding had a Shore A hardness of 98 after storage at 23° C. for 24 hours. The adhesion between polystyrene and the PU embedding composition was extremely strong so that they could no longer be separated. Adhesion as strong as this between polystyrene and conventional PU polyether-polyol embedding compositions has not been found.

EXAMPLE 6

Preparation of an MDI Mixture Modified with Urethane Groups

The procedure was similar to that described in Example 4 but the 219.83 parts by weight of polyoxypropylene-polyol were replaced by 218.15 parts by weight of a trimethylolpropane-started polyoxypropylene (80% by weight)/polyoxyethylene (20% by weight)-polyol with a hydroxyl number of 152 and a potassium ion content of 3 ppm.

The resulting MDI mixture modified with urethane groups had an NCO content of 20.2% by weight and a viscosity of 3266 mPa.s at 25° C.

EXAMPLE 7

Preparation of the PU Embedding Composition

A Component

Mixture of
- 7 parts by weight of a polyether-polyol with a hydroxyl number of 923 and a potassium ion content of 534 ppm, prepared by addition of ethylene oxide onto trimethylolpropane as starter in the presence of potassium hydroxide as catalyst,
- 92.95 parts by weight of a trimethylolpropane-started polyoxypropylene (80% by weight)/polyoxyethylene (20% by weight)-polyol with a hydroxyl number of 152 and a potassium ion content of 3 ppm and
- 0.05 part by weight of a catalyst composed of, based on the total weight, 94% by weight di-n-octyltin bis(2-ethylhexyl thioglycolate) and 6% by weight of mono-n-octyltin tris(2-ethylhexyl thioglycolate)

B component: MDI mixture modified with urethane groups from Example 6

100 parts by weight of A component and 80.01 parts by weight of B component, corresponding to an NCO index of 105, were vigorously mixed at 23° C.; the reaction mixture was poured into a polystyrene beaker and left to cure.

The reaction mixture had a potassium ion content of 37.4 ppm and a gel time of 124 seconds. The molding had a Shore A hardness of 96 after storage at 23° C. for 24 hours. The adhesion of the PU embedding compositions to polystyrene was so strong that the components could no longer be separated. Storage of the molding at 23° C. in 7% by weight aqueous peracetic acid for 10 days showed no decrease in the peracetic acid content.

EXAMPLE 8

Preparation of a PU Embedding Composition

A Component

Mixture of
- 11.1 parts by weight of a polyether-polyol with a hydroxyl number of 657 and a potassium ion content of 482 ppm, prepared by addition of propylene oxide and then ethylene oxide, in the ratio 47:53 by weight, onto a starter mixture of pentaerythritol and trimethylolpropane in the molar ratio 1:1,
- 88.85 parts by weight of a trimethylolpropane-started polyoxypropylene-polyol with a hydroxyl number of 148.5 and a potassium ion content of 3 ppm and
- 0.05 part by weight of a catalyst composed of, based on the total weight, 94% by weight di-n-octyltin bis(2-ethylhexyl thioglycolate) and 6% by weight mono-n-octyltin tris(2-ethylhexyl thioglycolate).

B component: MDI mixture modified with urethane groups, with an NCO content of 20.23% by weight, prepared as described in Example 4.

100 parts by weight of A component and 79.14 parts by weight of B component, corresponding to an NCO index of 105, were vigorously mixed at 23° C.; the reaction mixture was poured into a polystyrene beaker and left to cure.

The reaction mixture had a potassium ion content of 53.5 ppm and a gel time of 177 seconds.

The molding had a Shore A hardness of 96 after storage at 23° C. for 24 hours. The adhesion between polystyrene and the PU embedding composition was excellent.

EXAMPLE 9

Preparation of a PU Embedding Composition

A component

Mixture of
- 7 parts by weight of a polyether-polyol with a hydroxyl number of 923 and a potassium ion content of 534 ppm, prepared by addition of ethylene oxide onto trimethylolpropane in the presence of potassium hydroxide as catalyst,
- 92.992 parts by weight of a trimethylolpropane-started polyoxypropylene (80% by weight)-/polyoxyethylene (20% by weight)-polyol with a hydroxyl number of 152 and a potassium content of 3 ppm and
- 0.008 part by weight of dibutyltin dilaurate.

B component: MDI mixture modified with urethane groups from Example 6.

100 parts by weight of A component and 80.03 parts by weight of B component, corresponding to an NCO index of 105, were vigorously mixed at 23° C. The reaction mixture was poured into a polystyrene beaker and left to cure.

The reaction mixture had a potassium ion content of 37.4 ppm and a gel time of 234 seconds.

The molding had a Shore A hardness of 96 after storage at 23° C. for 24 hours. The adhesion between the PU embedding composition and polystyrene was excellent.

EXAMPLE 10

Preparation of a PU Embedding Composition

A Component

Mixture of
- 7 parts by weight of a polyether-polyol with a hydroxyl number of 923 and a potassium ion content of 534 ppm, prepared by addition of ethylene oxide onto trimethylolpropane in the presence of potassium hydroxide as catalyst, and parts by weight of a trimethylolpropane-started polyoxypropylene (80% by weight)/polyoxyethylene (20% by weight)-polyol with a hydroxyl number of 152 and a potassium content of 3 ppm.

B component: MDI mixture modified with urethane groups from Example 6.

100 parts by weight of A component and 80.04 parts by weight of B component, corresponding to an NCO index of 105, were vigorously mixed at 23° C. The reaction mixture was poured into a polystyrene beaker and left to cure.

The reaction mixture had a potassium ion content of 37.4 ppm and a gel time of 520 seconds.

The molding had a Shore A hardness of 91 after storage at 23° C. for 24 hours. The adhesion between the PU embedding composition and polystyrene was satisfactory.

EXAMPLE 11

Preparation of the Modified MDI 91.8 parts by weight of a urethane-containing MDI prepolymer with an NCO content of 23% by weight, which was prepared by reacting 4,4'-MDI with a mixture of dipropylene glycol and a polyoxypropylene glycol with a hydroxyl number of 250 and a potassium ion content of 3 ppm in the ratio 1:0.6 by weight, were heated to 60° C. with stirring and mixed dropwise over the course of 30 minutes with 8.2 parts by weight of a trimethylolpropanestarted polyoxyethylene (95% by weight)/polyoxypropylene (5% by weight)-polyol with a hydroxyl number of 100 and a potassium ion content of 3 ppm. The reaction mixture was heated at 80° C. for one hour, when the reaction was complete.

The resulting MDI mixture modified with urethane groups had an NCO content of 20.15% by weight and a viscosity of 2414 mPa.s at 25° C.

EXAMPLE 12

Preparation of the PU Embedding Composition

A component: from Example 10
B component: modified MDI mixture from Example 11

100 parts by weight of A component and
80.75 parts by weight of B component, corresponding to an NCO index of 105, were vigorously mixed at 23° C. The reaction mixture was poured into a polystyrene beaker and left to cure.

The reaction mixture had a potassium ion content of 69.4 ppm and a gel time of 173 seconds.

The molding had a Shore A hardness of 75 after storage at 23° C. for 24 hours. The adhesion between the PU embedding composition and polystyrene was satisfactory.

EXAMPLE 13

Preparation of the PU Embedding Composition

A component: as in Example 5 but catalyst content only 0.02 part by weight.
B component: as in Example 4
100 parts by weight of A component and
79.18 parts by weight of B component, corresponding to an NCO index of 105, were each degassed and heated to 40° C. and mixed in a low-pressure machine, and the reaction mixture was centrifuged at 40° C. for 5 minutes.

The molding produced by the centrifugal process was bubble-free and dry immediately after demolding and could be cut after 2 hours.

Dialyzers produced from polycarbonate sleeves, polysulfone hollow fibers and PU embedding compositions could be autoclaved at 121° C. at least 6 times without damaging the molding. Furthermore, storage of the molding at 23° C. in 7% by weight aqueous peracetic acid for 10 days showed no decrease in the peracetic acid content. The cytotoxicity test specified in the Guideline ISO/TR 7405-1984(E) was passed.

We claim:

1. A transparent, autoclavable, non-cytotoxic, essentially compact polyurethane embedding composition, prepared by reacting
   a) urethane group-containing diphenylmethane diisocyanate having an NCO content of from 29 to 15% by weight with
   b) compounds with at least two reactive hydrogens in the presence or absence of
   c) catalysts wherein component (b) is at least one polyether-polyol (b1) with an average functionality of from 3 to 8, a hydroxyl number of from 200 to 1000 and an alkali ion content of from 150 to 1200 ppm.

2. A transparent, autoclavable, non-cytotoxic, essentially compact polyurethane embedding composition, prepared by reacting
   a) urethane group-containing diphenylmethane diisocyanates having an NCO content of from 29 to 15% by weight with
   b) compounds with at least two reactive hydrogens in the presence or absence of
   c) catalysts wherein component (b) is a mixture which contains
      b1) at least one polyether-polyol with an average functionality of from 3 to 8, a hydroxyl number of from 200 to 1000 and an alkali metal ion content of from 150 to 1200 ppm and
      b2) castor oil or at least one polyether-polyol with a functionality of from 2 to 3, a hydroxyl number of from 90 to 200 and an alkali metal ion content of less than 10 ppm or a mixture of castor oil and at least one of said polyether-polyols.

3. A transparent, autoclavable, non-cytotoxic, essentially compact polyurethane embedding composition as claimed in claim 2, wherein (b) is a mixture which contains, based on the total weight of (b1) and (b2),
   b1) from 1 to 20% by weight of at least one polyether-polyol with an average functionality of from 3 to 8, a hydroxyl number of from 200 to 1000 and an alkali metal ion content of from 150 to 1200 ppm and b2) from 99 to 80% by weight of castor oil or at least one polyether-polyol with a functionality of from 2 to 3, a hydroxyl number of from 90 to 200 and an alkali metal ion content of less than 10 ppm or a mixture of castor oil and at least one of said polyether-polyols.

4. A transparent, autoclavable, non-cytotoxic, essentially compact polyurethane embedding composition as claimed in claim 2, wherein component (b2) in the mixture is castor oil.

5. A transparent, autoclavable, non-cytotoxic, essentially compact polyurethane embedding composition as claimed in claim 2, wherein component (b2) in the mixture is a trifunctional polyether-polyol with a hydroxyl number of from 120 to 180 and an alkali metal ion content of less than 5 ppm.

6. A transparent, autoclavable, non-cytotoxic, essentially compact polyurethane embedding composition as claimed in claim 1 or 2, wherein the alkali metal ions in (b1) are potassium ions.

7. A transparent, autoclavable, non-cytofoxic, essentially compact polyurethane embedding composition as claimed in claim 1 or 2, wherein the polyether-polyol (b1) is a trimethylolpropane-started polyoxyethylenepolyol with a hydroxyl number in the range from 632 to 970 and a potassium ion content in the range from 400 to 600 ppm.

8. A transparent, autoclavable, non-cytotoxic, essentially compact polyurethane embedding composition as claimed in claim 1 or 2, wherein the polyether-polyol (b) is a glycerol- or trimethylolpropane- or glycerol-trimethylolpropane-started polyoxypropylene-polyol with a hydroxyl number in the range from 210 to 480 and a potassium ion content in the range from 400 to 600 ppm.

9. A transparent, autoclavable, non-cytotoxic, essentially compact polyurethane embedding composition as claimed in claim 1 or 2, wherein the polyether-polyol (b1) is composed of at least one polyoxypropylene-polyol with an average functionality of from 4 to 8 and a hydroxyl number of from 230 to 500, obtained using sucrose or sorbitol or mixtures of sucrose and sorbitol as starters, in the presence or absence of at least one costarter selected from the group consisting of water, propylene glycol, glycerol or mixtures of at least two of said costarters, with the proviso that the polyether-polyols have an alkali metal ion content of from 400 to 700 ppm.

10. A transparent, autoclavable, non-cytotoxic, essentially compact polyurethane embedding composition as claimed in claim 1 or 2, wherein the polyether-polyol (b1) is a polyoxypropylene- or polyoxyethylene-polyol or a mixture of these polyoxyalkylene-polyols with a hydroxyl number of from 450 to 750, obtained using pentaerythritol, a mixture of pentaerythritol and glycerol, a mixture of pentaerythritol and trimethylolpropane, or a mixture of pentaerythritol, glycerol and trimethylolpropane as starters, with the proviso that the polyether-polyols have an alkali metal ion content of from 150 to 800 ppm.

11. A transparent, autoclavable, non-cytotoxic, essentially compact polyurethane embedding composition as claimed in claim 1 or 2, wherein the urethane group-containing diphenylmethane diisocyanates (a) are NCO prepolymers which contain urethane groups and have an NCO content of from 24 to 15% by weight and are prepared by reacting, based on the total weight, at least 85% by weight of an NCO-containing prepolymer with an NCO content of from 29 to 21% by weight, which in turn is obtained by reacting 4,4'-diphenylmethane diisocyanate with dipropylene glycol or at least one polyoxypropylene glycol with a hydroxyl number of up to 400 or a mixture of dipropylene glycol and at least one polyoxypropylene glycol with a hydroxyl number of up to 400, and a maximum of 15% by weight of castor oil.

12. A transparent, autoclavable, non-cytotoxic, essentially compact polyurethane embedding composition as claimed in claim 1 or 2, wherein the urethane group-containing diphenylmethane diisocyanates (a) are NCO prepolymers which contain urethane groups and have an NCO content of from 24 to 15% by weight and are prepared by reacting, based on the total weight, at least 85% by weight of an NCO-containing prepolymer with an NCO content of from 29 to 21% by weight, which in turn is obtained by reacting 4,4'-diphenylmethane diisocyanate with dipropylene glycol or at least one polyoxypropylene glycol with a hydroxyl number of from 50 to 250 or a mixture of dipropylene glycol and at least one polyoxypropylene glycol with a hydroxyl number of from 50 to 250, and a maximum of 15% by weight of a polyoxyalkylene-polyol which is started with glycerol, trimethylolpropane or a mixture of glycerol and trimethylolpropane and has a hydroxyl number of from 90 to 200 and an alkali metal ion content of less than 10 ppm from the group of polyoxypropylene-, polyoxypropylene-polyoxyethylene and polyoxyethylene-polyoxypropylene-polyols.

13. A transparent, autoclavable, non-cytotoxic, essentially compact polyurethane embedding composition as claimed in claim 1 or 2, wherein components (a) and (b) have a total alkali metal ion content of from 8 to 110 ppm.

14. A transparent, autoclavable, non-cytotoxic, essentially compact polyurethane embedding composition as claimed in claim 1 or 2, wherein components (a) and (b) have a total potassium ion content of from 8 to 110 ppm.

15. A transparent, autoclavable, non-cytotoxic, essentially compact polyurethane embedding composition as claimed in claim 1 or 2, wherein the catalyst (c) is mono-n-octyltin tris(2-ethylhexyl thioglycolate), di-n-octyltin bis(2-ethylhexyl thioglycolate) or dibutyltin dilaurate.

16. A transparent, autoclavable, non-cytotoxic, essentially compact polyurethane embedding composition as claimed in claim 1 or 2, wherein the catalyst (c) is a combination composed, based on the total weight, of from 1 to 99% by weight of mono-n-octyltin tris(2-ethylhexyl thioglycolate) and from 99 to 1% by weight of di-n-octyltin bis(2-ethylhexyl thioglycolate).

17. A transparent, autoclavable, non-cytotoxic, essentially compact polyuretane embedding composition as claimed in claim 1 or 2, wherein the catalyst (c) is a combination composed, based on the total weight, of 94% by weight of di-n-octyltin bis(2-ethylhexyl thioglycolate) and 6% by weight of mono-n-octyltin tris (2-ethylhexyl thioglycolate).

18. A process for preparing transparent, autoclavable, non-cytotoxic, essentially compact polyurethane embedding compositions by reacting
a) urethane group-containing diphenylmethane diisocyanates having an NCO content of from 29 to 15% by weight with
b) compounds with at least two reactive hydrogens in the presence or absence of
c) catalysts wherein component (b) is at least one polyether-polyol (b1) with an average functionality of from 3 to 8, a hydroxyl number of from 200 to 1000 and an alkali metal ion content of from 150 to 1200 ppm.

19. A process for preparing transparent, autoclavable, non-cytotoxic, essentially compact polyurethane embedding compositions by reacting
a) urethane group-containing diphenylmethane diisocyanates having an NCO content of from 29 to 15% by weight with
b) compounds with at least two reactive hydrogens in the presence or absence of
c) catalysts wherein component (b) is a mixture which contains
b1) at least one polyether-polyol with an average functionality of from 3 to 8, a hydroxyl number of from 200 to 1000 and an alkali metal ion content of from 150 to 1200 ppm and
b2) castor oil or at least one polyether-polyol with a functionality of from 2 to 3, a hydroxyl number of from 90 to 200 and an alkali metal ion content of less than 10 ppm or a mixture of castor oil and at least one of said polyether-polyols 20. A process as claimed in claim 19, wherein component (b) is a mixture which contains, based on the total weight of (b1) and (b2),
b1) from 1 to 30% by weight of at least one polyether-polyol with an average functionality of from 3 to 8, a hydroxyl number of from 200 to 1000 and an alkali metal ion content of from 150 to 1200 ppm and
b2) from 99 to 80% by weight of castor oil or at least one polyether-polyol with a functionality of from 2 to 3, a hydroxyl number of from 90 to 200 and an alkali metal ion content of less than 10 ppm or a mixture of castor oil and at least one of said polyether-polyols.

21. A process as claimed in claim 18 or 19, wherein the amounts of components (a) and (b) are such that the isocyanate index is in the range from 100 to 130.

22. Use of the transparent, autoclavable, non-cytotoxic, essentially compact polyurethane embedding compositions as claimed in claim 1 or 2 for embedding hollow polysulfone or polycarbonate fibers in dialysis equipment, for producing articles used in medicine, and for bonding bioceramic coatings to endoprostheses.

* * * * *